(12) United States Patent
Naidu et al.

(10) Patent No.: US 9,944,656 B2
(45) Date of Patent: Apr. 17, 2018

(54) BENZOTHIAZOLE MACROCYCLES AS INHIBITORS OF HUMAN IMMUNODEFICIENCY VIRUS REPLICATION

(71) Applicant: VIIV HEALTHCARE UK (No.5) LIMITED, Brentford, Middlesex (GB)

(72) Inventors: B. Narasimhulu Naidu, Wallingford, CT (US); Manoj Patel, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 81 days.

(21) Appl. No.: 15/115,790

(22) PCT Filed: Feb. 11, 2015

(86) PCT No.: PCT/US2015/015307
§ 371 (c)(1),
(2) Date: Aug. 1, 2016

(87) PCT Pub. No.: WO2015/123230
PCT Pub. Date: Aug. 20, 2015

(65) Prior Publication Data
US 2017/0008912 A1    Jan. 12, 2017

Related U.S. Application Data

(60) Provisional application No. 61/938,856, filed on Feb. 12, 2014.

(51) Int. Cl.
C07D 513/16    (2006.01)
C07D 513/22    (2006.01)
C07D 515/22    (2006.01)

(52) U.S. Cl.
CPC ......... C07D 513/22 (2013.01); C07D 513/16 (2013.01); C07D 515/22 (2013.01)

(58) Field of Classification Search
None
See application file for complete search history.

(56) References Cited

U.S. PATENT DOCUMENTS

2013/0281434 A1    10/2013    Babaoglu et al.

FOREIGN PATENT DOCUMENTS

WO    WO 2012/145728 A1    10/2012
WO    WO 2014/159959 A1    10/2014

*Primary Examiner* — Noble E Jarrell
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

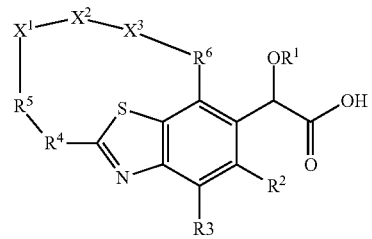

11 Claims, No Drawings

BENZOTHIAZOLE MACROCYCLES AS INHIBITORS OF HUMAN IMMUNODEFICIENCY VIRUS REPLICATION

CROSS-REFERENCE TO RELATED APPLICATIONS

This application is a 371 of International Application No. PCT/US2015/015307, filed 11 Feb. 2015, which claims the benefit of U.S. Provisional Application No. 61/938,856, filed 12 Feb. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963, WO2012066442 and WO2012140243, WO2013012649, WO2013043553, WO2013073875, WO2013134113, WO 2013134142, WO2014021867, WO20140028384, and WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

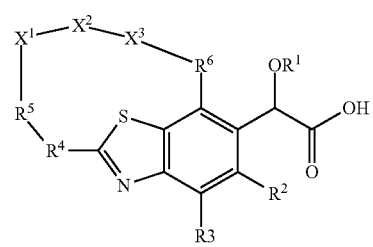

where:
$R^1$ is hydrogen, alkyl, or cycloalkyl;
$R^2$ is hydrogen or alkyl;
$R^3$ is hydrogen, alkyl or halo;
$R^4$ is ($R^7$)-piperazinyl or $Ar^1$;
$R^5$ is absent or $Ar^2$;
or $R^5$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, or oxetanyl;
$R^6$ is cycloalkyl or $Ar^3$;
$R^7$ is hydrogen or alkyl;
$Ar^1$ is phenyl, pyridinyl, pyrazinyl, pyrimidinyl, pyridazinyl, indazolyl, triazolyl, or quinolinyl, and is substituted with 0-3 alkyl substituents;

Ar² is phenyl, pyridinyl, ((R⁷)-piperazinyl)pyridinyl, pyrazinyl, pyrimidinyl, pyridazinyl, indazolyl, pyrazolopyridinyl, benzotriazolyl, quinolinyl, or aminoquinolinyl, and is substituted with 0-3 alkyl substituents;
Ar³ is phenyl, chromanyl, or dihydrobenzoxazinyl, and is substituted with 0-3 substituents selected from cyano, halo, alkyl, haloalkyl, alkoxy, and haloalkoxy;
$X^1$ is CH, CH₂, O, S, or NR⁷;
$X^2$ is alkylene or alkenylene; and
$X^3$ is CH, CH₂, CH₂O, O, S, or NR⁵;
or a pharmaceutically acceptable salt thereof.
Another aspect of the invention is a compound of Formula I where R¹ is alkyl; R² is alkyl; R³ is hydrogen; R⁴ is Ar¹; R⁶ is chromanyl; $X^1$ is CH₂, O, or NR⁷; $X^2$ is alkylene; and $X^3$ is CH₂; or a pharmaceutically acceptable salt thereof.
Another aspect of the invention is a compound of Formula I where R¹ is alkyl, R² is alkyl and R³ is hydrogen.
Another aspect of the invention is a compound of Formula I where R⁴ is Ar¹.
Another aspect of the invention is a compound of Formula I where R⁵ is Ar².
Another aspect of the invention is a compound of Formula I where R⁵ is (R⁷)-piperazinyl.
Another aspect of the invention is a compound of Formula I where Ar³ is chromanyl.
Another aspect of the invention is a compound of Formula I where $X^1$ is CH₂, O, or NR⁷; $X^2$ is alkylene; and $X^3$ is CH₂.
Another aspect of the invention is a compound of Formula I where $X^1$ is CH₂ or O; $X^2$ is alkylene or alkenylene; and $X^3$ is CH, CH₂ or O.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —CH₂CH₂CH₂O—. "Alkenyleneoxy" means a straight or branched divalent alkeneoxy group composed of 2 to 6 carbons with at least one double bond, for example, —CH═CHCH₂O—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC 18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$(Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | EC$_{50}$ μM |
|---|---|
| 1 | 5.624 |
| 2 | 0.350 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H"

for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1, I-2 and I-4 are synthesized by reactions known in the art. Palladium mediated coupling of intermediates I-1 and I-2 by procedure known in the art or as set forth in the examples below provided intermediates I-3. Reaction of intermediates I-3 with intermediates I-4 using conditions known to those skilled in the art furnished intermediates I-5. Intermediates I-5 were converted to intermediates I-6 by conditions known in the art, including ring closing metathesis. Hydrolysis of intermediates I-6 provided products I-7 which were converted to I-8 using conditions known in the art.

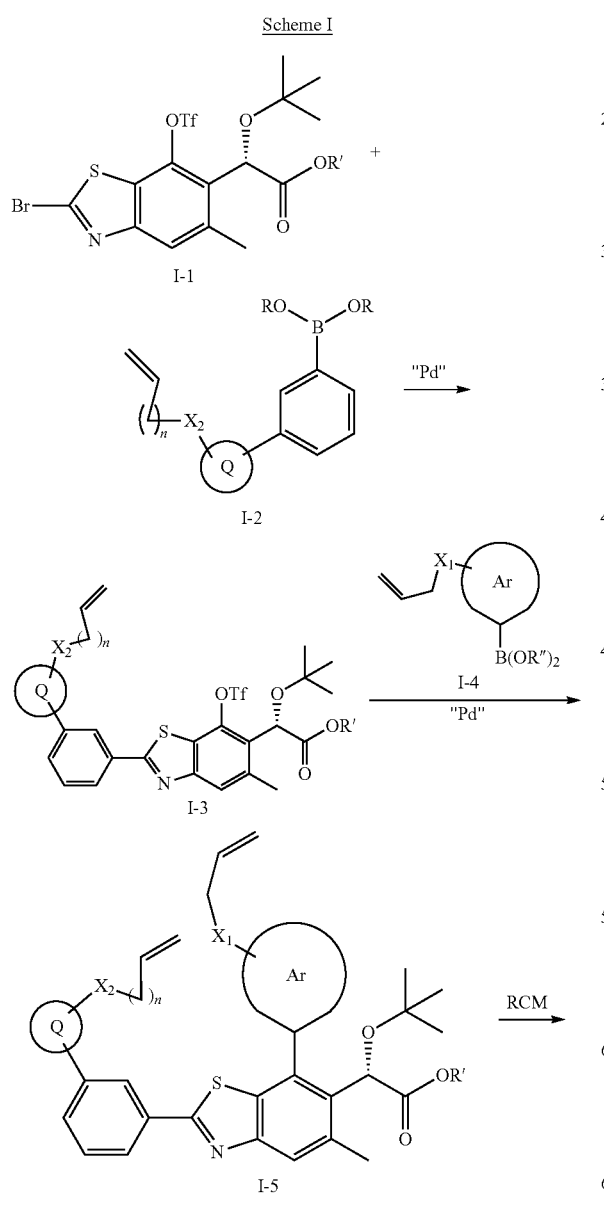

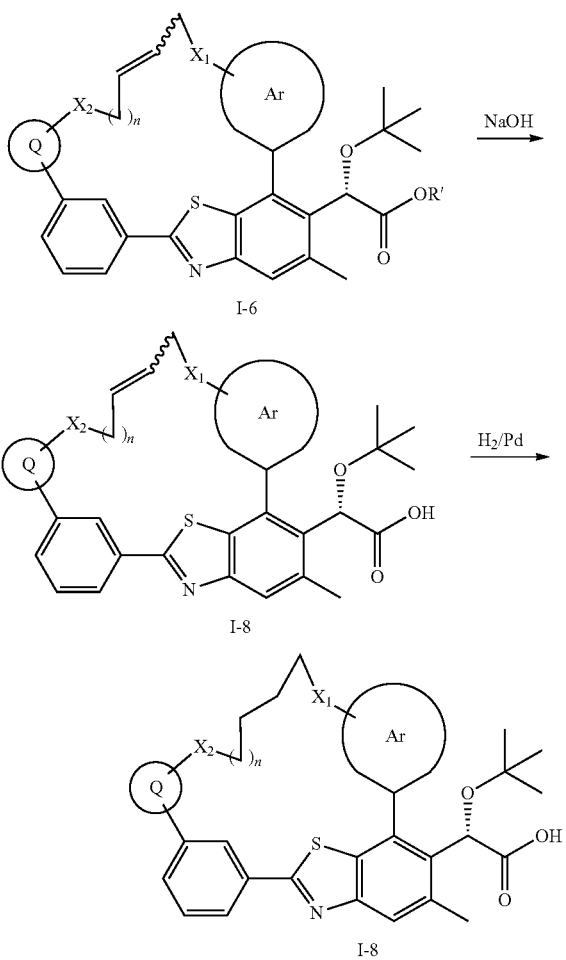

Intermediates II-1 can be transformed to final compounds II-6 and II-7 by methods known in the art as outlined in Scheme II.

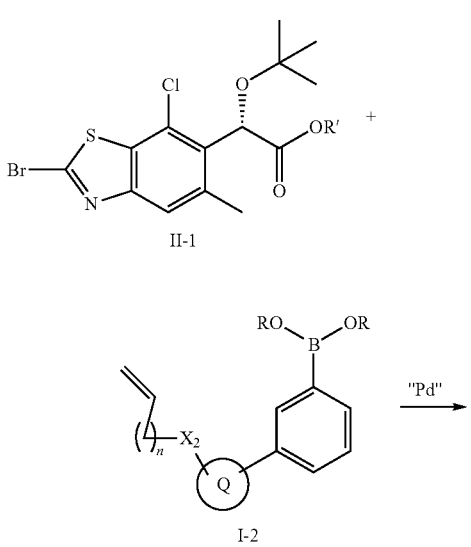

-continued

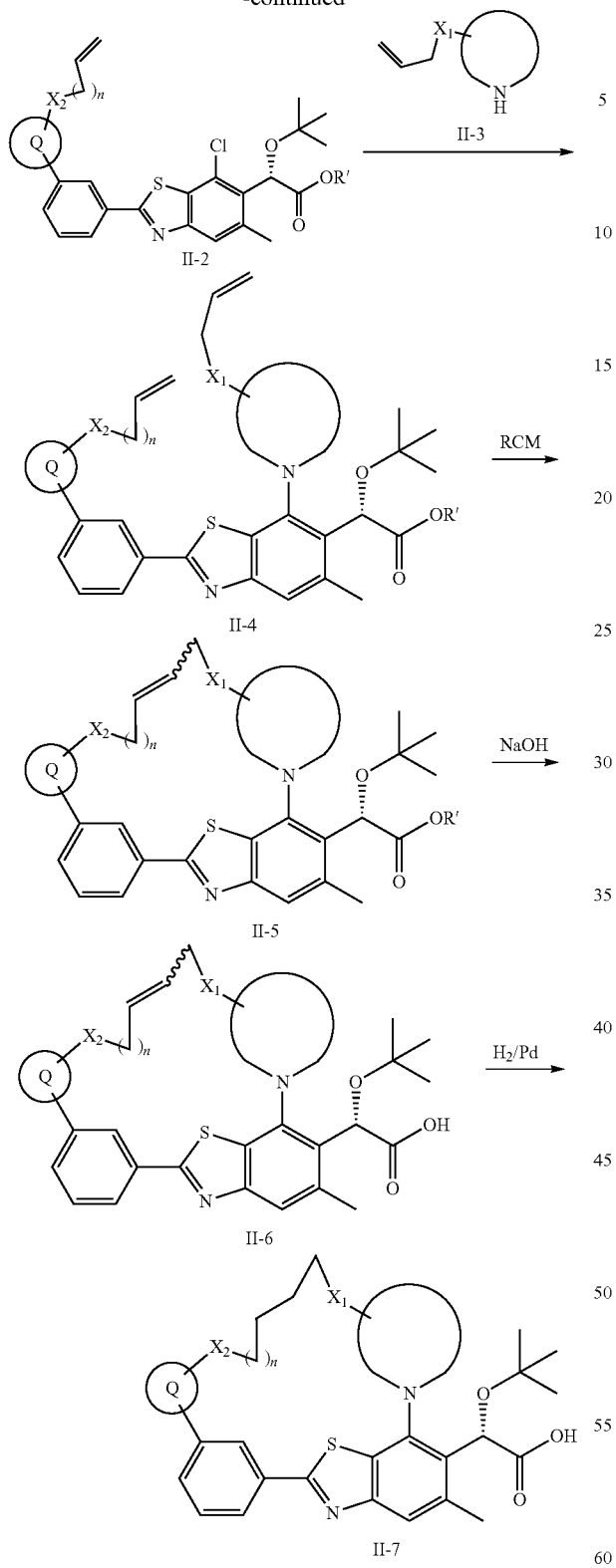

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H₂O/acetonitrile with 10 mM NH₄OAc and mobile phase B:A: 9:1 acetonitrile/H₂O with: 10 mM NH₄OAc or mobile phase A: 95:5 H₂O/MeOH with 20 mM NH₄OAc and mobile phase B: 95:5 MeOH/H₂O with 20 mM NH₄OAc.

Intermediate 1

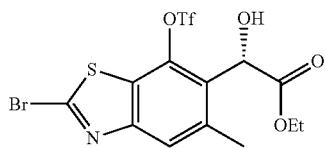 [SMILES: CCOC(=O)[C@@H](O)c1c(C)cc2nc(Br)sc2c1OS(=O)(=O)C(F)(F)F]

(S)-Ethyl 2-(2-bromo-5-methyl-7-(((trifluoromethyl)sulfonyl)oxy)benzo[d]thiazol-6-yl)-2-hydroxyacetate To a stirred yellow solution of ethyl 2-(2-bromo-5-methyl-7-(((trifluoromethyl)sulfonyl)oxy)benzo[d]thiazol-6-yl)-2-oxoacetate (2.5 g, 5.25 mmol, ref. WO2012145728) in anhydrous toluene (50 mL) was added 1M (R)-1-methyl-3,3-diphenylhexahydropyrrolo[1,2-c][1,3,2]oxazaborole/toluene (2.100 mL, 2.100 mmol). The mixture was cooled to −35° C. and a 50% solution of catechoborane/toluene (1.800 mL, 7.35 mmol) was added over 5 min. After 30 min, the reaction mixture was slowly warmed to −15° C. and stirred for additional 2 h. and diluted with EtOAc (100 mL) and sat. Na₂CO₃ (50 mL). The mixture was stirred vigorously for 30 min, and the organic phase washed with sat Na₂CO₃ (2×50 mL), dried (Na₂SO₄), filtered, concentrated and the residue was purified by silica gel chromatography (5-100% EtOAc/hexane) to afford desired (S)-ethyl 2-(2-bromo-5-methyl-7-(((trifluoromethyl)sulfonyl)oxy)benzo[d]thiazol-6-yl)-2-hydroxyacetate (2 g, 4.18 mmol, 80% yield) as off-white solid. ¹H NMR (500 MHz, CDCl₃) δ 7.84 (s, 1H), 5.70 (d, J=2.4 Hz, 1H), 4.39-4.22 (m, 2H), 3.50 (d, J=2.5 Hz, 1H), 2.53 (s, 3H), 1.24 (t, J=7.2 Hz, 3H). LCMS (M+2H)=480.0.

Intermediate 2

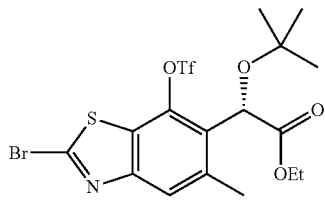 [SMILES: CCOC(=O)[C@@H](OC(C)(C)C)c1c(C)cc2nc(Br)sc2c1OS(=O)(=O)C(F)(F)F]

(S)-Ethyl 2-(2-bromo-5-methyl-7-(((trifluoromethyl)sulfonyl)oxy)benzo[d]thiazol-6-yl)-2-(tert-butoxy)acetate To a stirred solution of (S)-ethyl 2-(2-bromo-5-methyl-7-(((trifluoromethyl)sulfonyl)oxy)benzo[d]thiazol-6-yl)-2-hydroxyacetate (2 g, 4.18 mmol) in CH₂Cl₂ (25 mL) and t-Butyl acetate (17.50 mL) at rt was added 70% perchloric acid (1.078 mL, 12.55 mmol). After 3 h, the reaction mixture was diluted with CH₂Cl₂ (100 mL), carefully quenched with sat. NaHCO₃ (25 mL), organic layer separated and washed with brine (50 mL), dried (Na₂SO₄), filtered and concentrated to give yellow liquid. This was purified by flash column chromatography on silica gel column using (5-30% EtOAc/Hex as eluant) to afford the desired (S)-ethyl 2-(2-bromo-5-methyl-7-(((trifluoromethyl)sulfonyl)oxy)benzo[d]thiazol-6-yl)-2-(tert-butoxy)acetate (1.1 g, 2.059 mmol, 49.2% yield) as viscous oil. ¹H NMR (500 MHz, CDCl₃) δ 7.81 (s, 1H), 5.62 (s, 1H), 4.29-4.07 (m, 2H), 2.58 (d, J=0.6 Hz, 3H), 1.23 (s, 9H), 1.19 (t, J=7.1 Hz, 3H). LCMS (M+2H)=536.1.

Intermediate 3

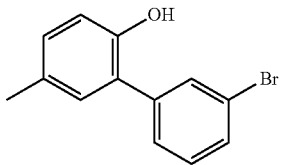

3'-Bromo-5-methyl-[1,1'-biphenyl]-2-ol

A mixture of 1-bromo-3-iodobenzene (3.72 g, 13.16 mmol), (2-hydroxy-5-methylphenyl)boronic acid (2 g, 13.16 mmol) and 2M Na₂CO₃ (13.16 mL, 26.3 mmol) in DMF (1 mL) was degassed for 10 min. Then, tetrakis(triphenylphosphine)palladium(0) (1.217 g, 1.053 mmol) was added, degassed for 5 min and heated at 90° C. for 16 h. Then, cooled, diluted with ether (100 mL), washed with water and brine (50 mL each), dried (MgSO₄), filtered and concentrated to give crude which was purified by Biotage (0-20% EtOAc/hexane) to afford 3'-bromo-5-methyl-[1,1'-biphenyl]-2-ol (2.2 g, 8.36 mmol, 63.5% yield) as light yellow liquid. ¹H NMR (500 MHz, CDCl₃) 7.67 (t, J=1.8 Hz, 1H), 7.56-7.52 (m, 1H), 7.47-7.44 (m, 1H), 7.37 (d, J=7.7 Hz, 1H), 7.12-7.08 (m, 1H), 7.06 (d, J=2.0 Hz, 1H), 6.89 (d, J=8.0 Hz, 1H), 4.92 (s, 1H), 2.35 (s, 3H).

Intermediate 4

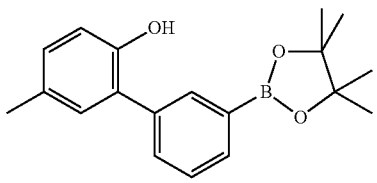

5-Methyl-3'-(4,4,5,5-tetramethyl-1,3,2-dioxaborolan-2-yl)[1,1'-biphenyl]-2-ol

A mixture of 3'-bromo-5-methyl-[1,1'-biphenyl]-2-ol (200 mg, 0.760 mmol), bis(pinacolateo)diboron (203 mg, 0.798 mmol) and KOAc (224 mg, 2.280 mmol) in 1,4-dioxane (8 mL) was sparged with N2 for 15 min. Then, 1,1-bis(diphenylphosphino)ferrocene]dichloropalladium(II) CH₂Cl₂ complex (31.0 mg, 0.038 mmol) was added, sparged for additional 5 min and heated at 95° C. for 2 h. Then, cooled, diluted with Et₂O (250 mL), washed with water (4×50 mL), brine (25 mL), dried (MgSO₄), filtered and concentrated to give brow paste which was purified by flash chromatography (5-25% EtOAc/hexane) to afford 5-methyl-3'-(4,4,5,5-tetramethyl-1,3,2-dioxaborolan-2-yl)-[1,1'-biphenyl]-2-ol (190 mg, 0.613 mmol, 81% yield) as viscous oil. ¹H NMR (500 MHz, CDCl₃) δ 7.92 (s, 1H), 7.85 (dt, J=7.3, 1.2 Hz, 1H), 7.58 (dt, J=7.7, 1.6 Hz, 1H), 7.51 (t, J=7.5 Hz, 1H), 7.11-7.04 (m, 2H), 6.89 (d, J=8.0 Hz, 1H), 5.01 (s, 1H), 2.34 (s, 3H), 1.38 (s, 12H). LCMS (M+H)=311.3.

Intermediate 5

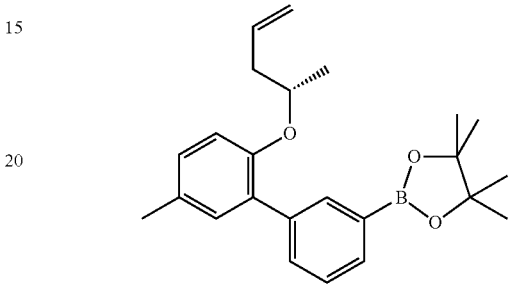

(S)-4,4,5,5-Tetramethyl-2-(5'-methyl-2'-(pent-4-en-2-yloxy)[1,1'-biphenyl]-3-yl)-1,3,2-dioxaborolane To a solution of 5-methyl-3'-(4,4,5,5-tetramethyl-1,3,2-dioxaborolan-2-yl)-[1,1'-biphenyl]-2-ol (1 g, 3.22 mmol) and (R)-pent-4-en-2-ol (0.833 g, 9.67 mmol) in THF (20 mL) was added Ph₃P (2.54 g, 9.67 mmol) followed by DEAD (1.531 mL, 9.67 mmol) and the resulting mixture was stirred at room temp for 16 h. Water was then added and the mixture was extracted with ether (2×50 mL), dried (Na₂SO₄), filtered and concentrated. The residue was then purified by Biotage (0-10% EtOAc/hexane) to afford (S)-4,4,5,5-tetramethyl-2-(5'-methyl-2'-(pent-4-en-2-yloxy)-[1,1'-biphenyl]-3-yl)-1,3,2-dioxaborolane (800 mg, 2.115 mmol, 65.6% yield) as viscous liquid. ¹H NMR (500 MHz, CDCl₃) δ 7.99 (s, 1H), 7.77 (dt, J=7.3, 1.2 Hz, 1H), 7.70 (dt, J=7.7, 1.6 Hz, 1H), 7.40 (t, J=7.5 Hz, 1H), 7.20 (d, J=2.2 Hz, 1H), 7.11-7.04 (m, 1H), 6.89 (d, J=8.2 Hz, 1H), 5.79 (ddt, J=17.1, 10.2, 7.2 Hz, 1H), 5.09-5.01 (m, 2H), 4.27 (sxt, J=6.0 Hz, 1H), 2.40 (qd, J=7.0, 5.6 Hz, 1H), 2.35 (s, 3H), 2.27 (dt, J=14.1, 6.8 Hz, 1H), 1.38 (s, 12H), 11.19 (d, J=6.1 Hz, 3H). LCMS (M+H)=379.4.

Intermediate 6

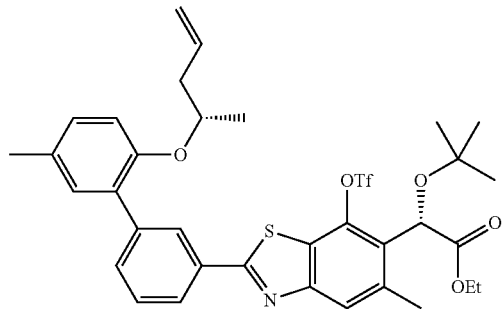 [SMILES: C=CC[C@H](C)Oc1ccc(C)cc1-c1cccc(-c2nc3cc(C)c([C@H](OC(C)(C)C)C(=O)OCC)c(OS(=O)(=O)C(F)(F)F)c3s2)c1]

(S)-Ethyl 2-(tert-butoxy)-2-(5-methyl-2-(5'-methyl-2'-((S)-pent-4-en-2-yloxy)-[1,1'-biphenyl]-3-yl)-7-(((trifluoromethyl)sulfonyl)oxy)benzo[d]thiazol-6-yl)acetate To a mixture of (S)-ethyl 2-(2-bromo-5-methyl-7-(((trifluoromethyl)sulfonyl)oxy)benzo[d]thiazol-6-yl)-2-(tert-butoxy)acetate (439 mg, 0.822 mmol), (S)-4,4,5,5-tetramethyl-2-(5'-methyl-2'-(pent-4-en-2-yloxy)-[1,1'-biphenyl]-3-yl)-1,3,2-dioxaborolane (311 mg, 0.822 mmol) and $K_2CO_3$ (341 mg, 2.465 mmol) in Toluene (6 mL), ethanol (3 mL) and water (3 mL) was added tetrakis(triphenylphosphine)palladium(0) (95 mg, 0.082 mmol) and the resulting mixture was heated at 90° C. for 3 h. After cooling to room temp, water was added and the mixture was extracted with ether (2×25 mL), dried ($Na_2SO_4$), filtered and concentrated. The residue was then purified by Biotage (0-30% EtOAc/hexane) to afford (S)-ethyl 2-(tert-butoxy)-2-(5-methyl-2-(5'-methyl-2'-((S)-pent-4-en-2-yloxy)-[1,1'-biphenyl]-3-yl)-7-(((trifluoromethyl)sulfonyl)oxy)benzo[d]thiazol-6-yl)acetate (500 mg, 0.708 mmol, 86% yield) as off-white solid. $^1$H NMR (500 MHz, $CDCl_3$) δ 8.28 (t, J=1.7 Hz, 1H), 8.09-8.01 (m, 1H), 7.92 (s, 1H), 7.72 (dt, J=7.7, 1.4 Hz, 1H), 7.56-7.49 (m, 1H), 7.25 (d, J=1.9 Hz, 1H), 7.16 (dd, J=8.4, 1.7 Hz, 1H), 6.98-6.89 (m, 1H), 5.79 (ddt, J=17.1, 10.1, 7.1 Hz, 1H), 5.67 (s, 1H), 5.09-4.96 (m, 2H), 4.39 (sxt, J=6.1 Hz, 1H), 4.28-4.12 (m, 2H), 2.62-2.57 (m, 3H), 2.45 (qd, J=7.0, 5.5 Hz, 1H), 2.39 (s, 3H), 2.31 (dt, J=14.0, 6.9 Hz, 1H), 1.27 (s, 3H), 1.26 (s, 9H), 1.20 (t, J=7.1 Hz, 3H). LCMS (M+H)= 706.25.

Intermediate 7

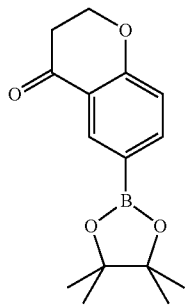 [SMILES: CC1(C)OB(c2ccc3c(c2)C(=O)CCO3)OC1(C)C]

6-(4,4,5,5-Tetramethyl-1,3,2-dioxaborolan-2-yl)chroman-4-one

A mixture of 6-bromochroman-4-one (3.75 g, 16.52 mmol), bis(pinacolato)diborane (4.40 g, 17.34 mmol) and KOAc (4.86 g, 49.5 mmol) in 1,4-dioxane (100 mL) was sparged with $N_2$ for 15 min. Then, 1,1-bis(diphenylphosphino)ferrocene]dichloropalladium(II) $CH_2Cl_2$ complex (0.674 g, 0.826 mmol) was added, sparged for 5 min and heated (95° C.) for 16 h. The reaction was cooled, diluted with $Et_2O$ (250 mL), washed with water (2×100 mL), brine (25 mL), dried ($MgSO_4$), filtered and concentrated. The residue was purified by biotage (120 g $SiO_2$, 0% (3 CV), 0-60% (15 CV), EtOAc in hexanes) to afford the desired product (3.626 g, 13.23 mmol, 80% yield) as an pale yellow viscous oil. $^1$H NMR (500 MHz, $CDCl_3$) δ 8.40 (d, J=1.6 Hz, 1H), 7.89 (dd, J=8.3, 1.7 Hz, 1H), 6.96 (dd, J=8.4, 0.3 Hz, 1H), 4.59-4.53 (m, 2H), 2.83 (dd, J=6.8, 6.1 Hz, 2H), 1.34 (s, 12H). LCMS (M+H)=275.15.

Intermediate 8

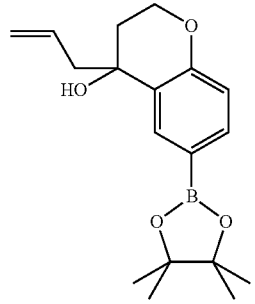 [SMILES: C=CCC1(O)CCOc2ccc(B3OC(C)(C)C(C)(C)O3)cc21]

4-Allyl-6-(4,4,5,5-tetramethyl-1,3,2-dioxaborolan-2-yl)chroman-4-ol

A cold (−78°) solution of 6-(4,4,5,5-tetramethyl-1,3,2-dioxaborolan-2-yl)chroman-4-one (1.21 g, 4.41 mmol) in dry THF (20 ml) was treated with 1.0 M allylmagnesium bromide in $Et_2O$ (6.62 ml, 6.62 mmol) by dropwise addition over 2 min. The reaction was stirred for 10 min, allowed to warm to room temperature and stirred for 90 min, then quenched with sat'd aq. $NH_4Cl$ (2 mL). The mixture was diluted with $Et_2O$ (50 mL), washed with water (10 mL), brine (10 mL), dried ($MgSO_4$), filtered and concentrated. The residue was purified by biotage (40 g $SiO_2$, 0% (3 CV), 0-60% (15 CV), EtOAc in hexanes) to afford the desired product (0.864 g, 2.73 mmol, 61.9% yield) as a colorless viscous oil. $^1$H NMR (400 MHz, $CDCl_3$) δ 7.94 (d, J=1.5 Hz, 1H), 7.64 (dd, J=8.2, 1.6 Hz, 1H), 6.83 (d, J=8.3 Hz, 1H), 5.81 (ddt, J=17.2, 10.2, 7.3 Hz, 1H), 5.21-5.17 (m, 1H), 5.15 (s, 1H), 4.29-4.24 (m, 2H), 2.84 (dd, J=14.1, 7.5 Hz, 1H), 2.66 (dd, J=14.1, 7.0 Hz, 1H), 2.14 (ddd, J=13.9, 7.9, 5.5 Hz, 1H), 2.01 (s, 1H), 2.00-1.91 (m, 1H), 1.34 (d, J=1.0 Hz, 12H). LCMS (M+H—$H_2O$)=299.2.

Intermediate 9

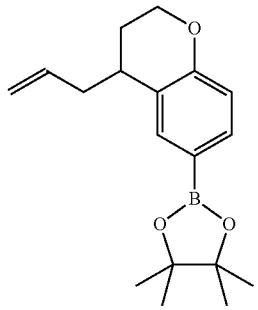 [SMILES: C=CCC1CCOc2ccc(B3OC(C)(C)C(C)(C)O3)cc21]

2-(4-Allylchroman-6-yl)-4,4,5,5-tetramethyl-1,3,2-dioxaborolane

A stirred solution of 4-allyl-6-(4,4,5,5-tetramethyl-1,3,2-dioxaborolan-2-yl)chroman-4-ol (1.80 g, 5.69 mmol) and triethylsilane (7.27 ml, 45.5 mmol) in DCE (30 ml) was treated with TFA (14.03 ml, 182 mmol) by rapid addition at ambient temperature. The reaction was stirred for 10 min, then carefully quenched with sat'd. aq. NaHCO$_3$ (200 mL). The organic layer was concentrated and the residue was purified by biotage (80 g SiO$_2$, 0% (3 CV), 0-60% (15 CV), 60% (2 CV), EtOAc in hexanes) to afford the desired product (0.942 g, 3.14 mmol, 55.1% yield) as a viscous clear oil. $^1$H NMR (400 MHz, CDCl$_3$) δ 7.64 (s, 1H), 7.56 (dd, J=8.2, 1.4 Hz, 1H), 6.80 (d, J=8.0 Hz, 1H), 5.90-5.76 (m, 1H), 5.15-5.04 (m, 2H), 4.23-4.14 (m, 2H), 2.89 (dq, J=10.0, 5.0 Hz, 1H), 2.75-2.62 (m, 1H), 2.35-2.22 (m, 1H), 2.09-1.96 (m, 1H), 1.92-1.81 (m, 1H), 1.34 (s, 12H). LCMS (M+H)=301.3.

Intermediate 10

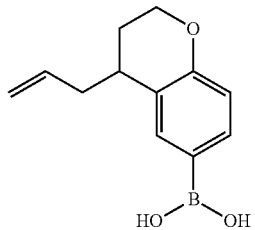 [SMILES: C=CCC1CCOc2ccc(B(O)O)cc21]

(4-Allylchroman-6-yl)boronic acid

To a mixture of 2-(4-allylchroman-6-yl)-4,4,5,5-tetramethyl-1,3,2-dioxaborolane (235 mg, 0.783 mmol) in THF (4 mL) and water was added sodium periodate (335 mg, 1.566 mmol) and the resulting mixture was heated at 60° C. for 16 h. Mixture was then cooled to room temp and 1N HCl (6 mL) was added and the mixture was stirred for 2 h. The mixture was then diluted with EtOAc (100 mL) and washed with brine (25 mL), dried (Na$_2$SO$_4$), filtered and concentrated to afford (4-allylchroman-6-yl)boronic acid (90 mg, 0.413 mmol, 52.7% yield) as white powder. Used as is in the next step without further purification.

Intermediate 11

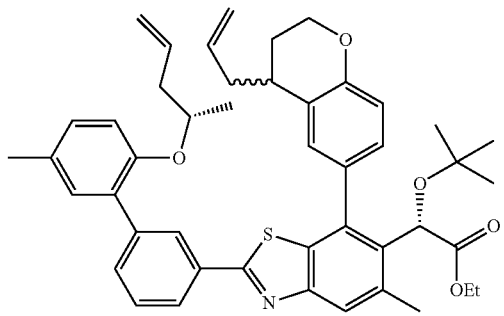 [SMILES: C=CCC1CCOc2ccc(-c3c([C@H](OC(C)(C)C)C(=O)OCC)c(C)cc4nc(-c5cccc(-c6cc(C)ccc6O[C@@H](C)CC=C)c5)sc34)cc21]

(2S)-Ethyl 2-(7-(4-allylchroman-6-yl)-5-methyl-2-(5'-methyl-2'-((S)-pent-4-en-2-yloxy)[1,1'-biphenyl]-3-yl)benzo[d]thiazol-6-yl)-2-(tert-butoxy)acetate To a solution of (S)-ethyl 2-(tert-butoxy)-2-(5-methyl-2-(5'-methyl-2'-((S)-pent-4-en-2-yloxy)-[1,1'-biphenyl]-3-yl)-7-(((trifluoromethyl)sulfonyl)oxy)benzo[d]thiazol-6-yl)acetate (200 mg, 0.283 mmol) in DME (5 mL) was added (4-allylchroman-6-yl)boronic acid (124 mg, 0.567 mmol), chloro(2-dicyclohexylphosphino-2',6'-di-i-propoxy-1,1'-biphenyl)[2-(2-aminoethylphenyl)]palladium(II), methyl-t-butylether adduct (23.15 mg, 0.028 mmol) (sphos palaldacycle) and cesium fluoride (172 mg, 1.133 mmol). The reaction mixture was then heated in microwave at 110° C. for 2 h. At this point LCMS indicated completion of reaction and desired product as major. Water (5 mL) was then added and the mixture was extracted with ether (25 mL), washed with brine (10 mL), dried (Na$_2$SO$_4$), filtered and concentrated. The residue was then purified by Biotage (0-20% EtOAc/hexane) to afford (2S)-ethyl 2-(7-(4-allylchroman-6-yl)-5-methyl-2-(5'-methyl-2'-((S)-pent-4-en-2-yloxy)-[1,1'-biphenyl]-3-yl)benzo[d]thiazol-6-yl)-2-(tert-butoxy)acetate (38 mg, 0.052 mmol, 18.37% yield) as viscous oil (in separable mixture of diastereomers). $^1$H NMR (500 MHz, CDCl$_3$) δ 8.20-8.18 (m, 1H), 8.05-8.01 (m, 1H), 7.86 (s, 1H), 7.69-7.64 (m, 1H), 7.49-7.45 (m, 1H), 7.42-7.31 (m, 2H), 7.22 (d, J=1.7 Hz, 1H), 7.12 (d, J=8.8 Hz, 1H), 6.98-6.90 (m, 2H), 5.84-5.70 (m, 2H), 5.36-5.27 (m, 1H), 5.15-4.94 (m, 5H), 4.37-4.16 (m, 6H), 2.63-2.59 (m, 4H), 2.37 (s, 3H), 2.32-2.21 (m, 2H), 2.19-2.09 (m, 1H), 2.01-1.87 (m, 1H), 1.30-1.24 (m, 3H), 1.21-1.18 (m, 3H), 1.02-0.98 (m, 9H). LCMS (M+H)=730.3.

Intermediate 12

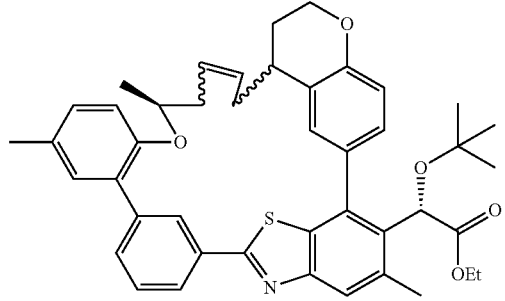 [SMILES: CCOC(=O)[C@@H](OC(C)(C)C)c1c(C)cc2nc3sc2c1-c1ccc2c(c1)C(CC=CC[C@H](C)Oc1ccc(C)cc1-c1cccc-3c1)CCO2]

Ethyl (2S)-2-(tert-butoxy)-2-[(22S)-4,17,22-trimethyl-21,30-dioxa-8-thia-37-azaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,15(20),16,18,24,31,34-tetradecaen-3-yl]acetate To a solution of (2S)-ethyl 2-(7-(4-allylchroman-6-yl)-5-methyl-2-(5'-methyl-2'-((S)-pent-4-en-2-yloxy)-[1,1'-biphenyl]-3-yl)benzo[d]thiazol-6-yl)-2-(tert-butoxy)acetate (4.43 mg, 6.06 µmol) in ClCH$_2$CH$_2$Cl (40 mL) at room temp was added (1,3-dimesitylimidazolidin-2-ylidene)(2-isopropoxybenzylidene)ruthenium(VI) chloride (38 mg, 0.061 mmol) and the resulting mixture was heated at 80° C. for 2 h. At this point LCMS indicated completion of reaction. Mixture was then cooled concentrated and purified by Biotage (0-30% EtOAc/hexane) to afford ethyl (2S)-2-(tert-butoxy)-2-[(22S)-4,17,22-trimethyl-21,30-dioxa-8-thia-37-azaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,15(20),16,18,24,31,34-tetradecaen-3-yl]acetate (28 mg, 0.040 mmol, 65.8% yield) as approx 1:1 inseparable mixture of cis and trans product. LCMS (M+H)=702.3.

Examples 1 and 2

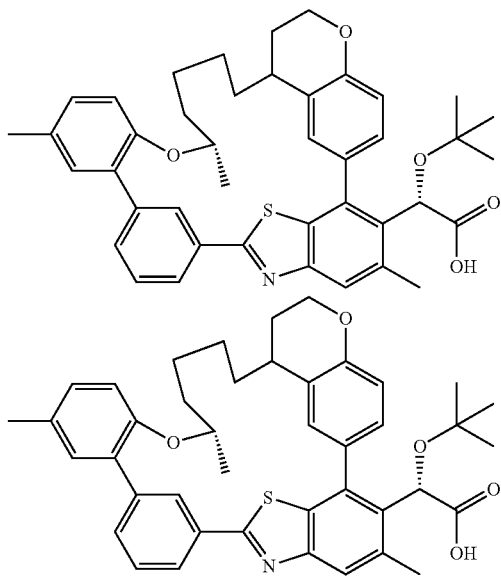

(2S)-2-(tert-Butoxy)-2-[(22S)-4,17,22-trimethyl-21,
30-dioxa-8-thia-37-azaheptacyclo[25.6.2.1$^{6,9}$.
1$^{10,14}$.0$^{2,7}$.0$^{15,20}$.0$^{31,35}$]heptatriaconta-1(33),2,4,6,9
(37),10(36),11,13,15(20),16,18,31,34-tridecaen-3-yl]
acetic acid To a solution of ethyl (2S)-2-(tert-butoxy)-2-[(22S)-4,17,
22-trimethyl-21,30-dioxa-8-thia-37-azaheptacyclo
[25.6.2.1$^{6,9}$.1$^{10,14}$.0$^{2,7}$.0$^{15,20}$.0$^{31,35}$]heptatriaconta-1(33),2,
4,6,9(37),10(36),11,13,15(20),16,18,24,31,34-tetradecaen-
3-yl]acetate (28 mg, 0.040 mmol) in ethanol (1 mL) was
added 10% Pd/C (4.25 mg, 3.99 μmol) and the resulting
mixture was stirred under hydrogen balloon atmosphere for
3 h. Mixture was then filtered and treated with 1N NaOH
(0.199 mL, 0.199 mmol) at 75° C. for 3 h. Mixture was then
cooled and purified by prep-HPLC to afford two diastereomers.

Diastereomer 1 (first eluting on HPLC) (6.6 mg, 9.77
μmol, 24.48% yield): $^1$H NMR (500 MHz, DMSO-d$_6$) δ
8.17 (s, 1H), 8.08 (d, J=7.3 Hz, 1H), 7.83 (s, 1H), 7.67-7.60
(m, 2H), 7.55 (br. s., 1H), 7.51 (s, 1H), 7.24 (s, 1H), 7.14 (d,
J=8.4 Hz, 1H), 7.03 (d, J=8.8 Hz, 1H), 6.92 (d, J=8.4 Hz,
1H), 5.23 (s, 1H), 4.48 (br. s., 1H), 4.28 (br. s., 1H), 4.09 (br.
s., 1H), 3.37 (br. s., 3H), 3.02 (br. s., 1H), 2.30 (s, 3H), 2.01
(br. s., 1H), 1.96 (br. s., 2H), 1.74 (d, J=12.5 Hz, 2H), 1.61
(br. s., 2H), 1.49 (br. s., 1H), 1.37 (d, J=11.0 Hz, 1H), 1.23
(br. s., 1H), 1.09-1.04 (m, 3H), 0.80 (s, 9H). LCMS (M+H)=
676.4.

Diastereomer 2 (second eluting on HPLC) (8.8 mg, 0.013
mmol, 32.6% yield). $^1$H NMR (500 MHz, DMSO-d$_6$) δ 8.22
(d, J=7.7 Hz, 1H), 8.13 (s, 1H), 7.86 (s, 1H), 7.61 (t, J=7.7
Hz, 1H), 7.56 (d, J=7.3 Hz, 1H), 7.21 (s, 1H), 7.13 (d, J=8.8
Hz, 1H), 7.09 (s, 1H), 7.04-6.99 (m, 2H), 6.84 (d, J=8.4 Hz,
1H), 5.20 (s, 1H), 4.45-4.33 (m, 1H), 4.26 (br. s., 2H), 3.91
(s, 1H), 2.74 (s, 2H), 2.61 (s, 3H), 2.28 (s, 3H), 2.12 (br. s.,
1H), 1.84 (d, J=13.6 Hz, 1H), 1.66 (d, J=5.9 Hz, 2H),
1.53-1.42 (m, 4H), 1.11 (s, 9H), 0.98 (d, J=5.9 Hz, 3H).
LCMS (M+H)=676.4.

The following examples could be prepared by a person
skilled in the art by following the procedures known in the
art or as set forth in the examples 1 and 2.

Example 3

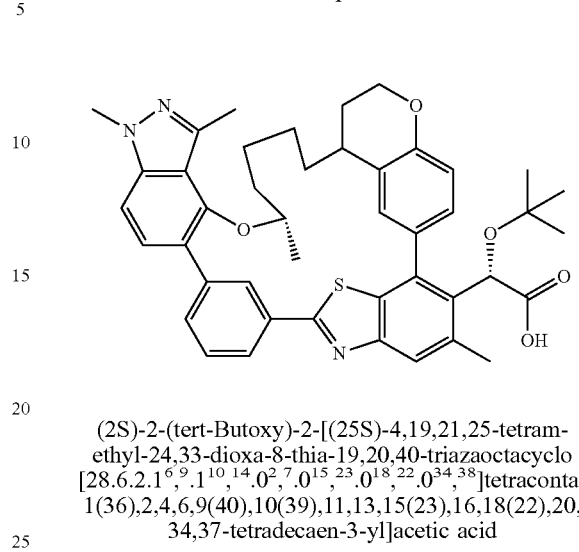

(2S)-2-(tert-Butoxy)-2-[(25S)-4,19,21,25-tetramethyl-24,33-dioxa-8-thia-19,20,40-triazaoctacyclo
[28.6.2.1$^{6,9}$.1$^{10,14}$.0$^{2,7}$.0$^{15,23}$.0$^{18,22}$.0$^{34,38}$]tetraconta-
1(36),2,4,6,9(40),10(39),11,13,15(23),16,18(22),20,
34,37-tetradecaen-3-yl]acetic acid

Example 4

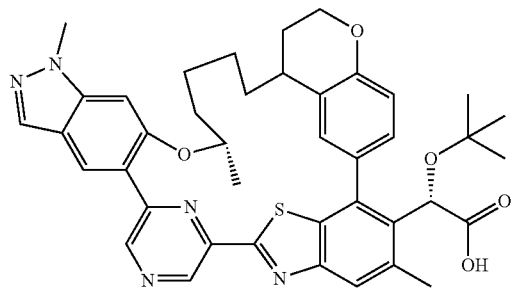

(2S)-2-(tert-Butoxy)-2-[(25S)-4,20,25-trimethyl-24,
33-dioxa-8-thia-12,19,20,39,40-pentaazaoctacyclo
[28.6.2.1$^{6,9}$.1$^{10,14}$.0$^{2,7}$.0$^{15,23}$.0$^{17,21}$.0$^{34,38}$]tetraconta-
1(36),2,4,6,9(40),10(39),11,13,15(23),16,18,21,34,
37-tetradecaen-3-yl]acetic acid

Example 5

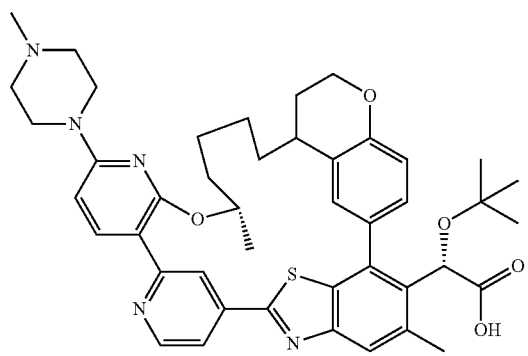 [SMILES: Cc1cc2nc3sc2c(c1[C@H](OC(C)(C)C)C(=O)O)-c1ccc2c(c1)C(CCCC[C@H](C)Oc1nc(N4CCN(C)CC4)ccc1-c1cc-3ccn1)CCO2]

21

(2S)-2-(tert-Butoxy)-21(22S)-4,22-dimethyl-18-(4-methylpiperazin-1-yl)-21,30-dioxa-8-thia-13,19,37-triazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,15(20),16,18,31,34-tridecaen-3-yl]acetic acid Example 6

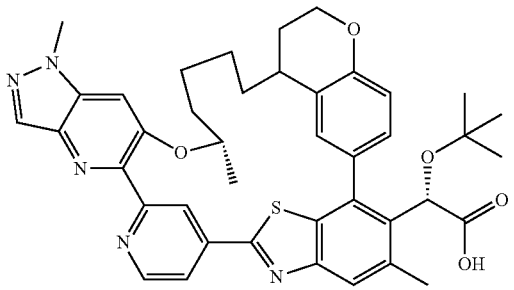 [SMILES: Cc1cc2nc3sc2c(c1[C@H](OC(C)(C)C)C(=O)O)-c1ccc2c(c1)C(CCCC[C@H](C)Oc1cc4c(cnn4C)nc1-c1cc-3ccn1)CCO2]

(2S)-2-(tert-Butoxy)-2-[(25S)-4,20,25-trimethyl-24,33-dioxa-8-thia-13,16,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid Example 7

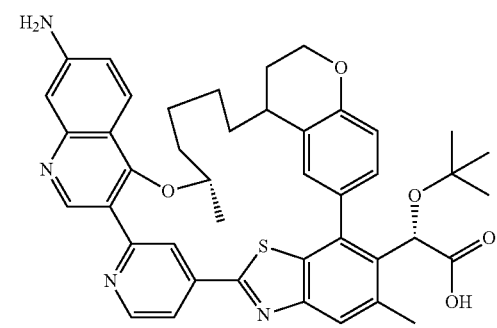 [SMILES: Cc1cc2nc3sc2c(c1[C@H](OC(C)(C)C)C(=O)O)-c1ccc2c(c1)C(CCCC[C@H](C)Oc1c(cnc4cc(N)ccc14)-c1cc-3ccn1)CCO2]

22

(2S)-2-[(26S)-20-Amino-4,26-dimethyl-25,34-dioxa-8-thia-13,17,41-triazaoctacyclo[29.6.2.1$^{6,9}$.1$^{10,14}$.0$^{2,7}$.0$^{15,24}$.0$^{18,23}$.0$^{35,39}$]hentetraconta-1(37),2,4,6,9(41),10(40),11,13,15(24),16,18(23),19,21,35,38-pentadecaen-3-yl]-2-(tert-butoxy)acetic acid Example 8

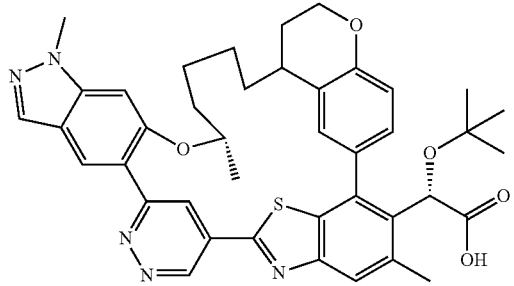

(2S)-2-(tert-Butoxy)-2-[(25S)-4,20,25-trimethyl-24,33-dioxa-8-thia-12,13,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid Example 9

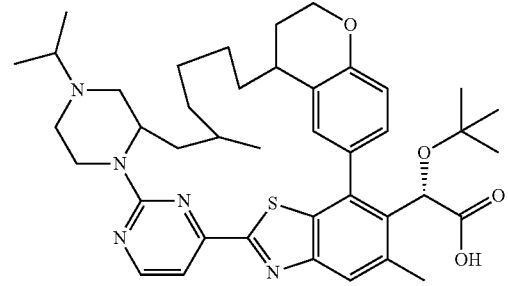 [SMILES: Cc1cc2nc3sc2c(c1[C@H](OC(C)(C)C)C(=O)O)-c1ccc2c(c1)C(CCCCC(C)CC1CN(C(C)C)CCN1c1nccc-3n1)CCO2]

(2S)-2-(tert-Butoxy)-2-[4,22-dimethyl-18-(propan-2-yl)-30-oxa-8-thia-13,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid Example 10

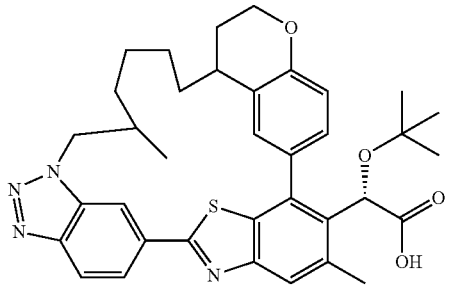 [SMILES: Cc1cc2nc3sc2c(c1[C@H](OC(C)(C)C)C(=O)O)-c1ccc2c(c1)C(CCCCC(C)Cn1nnc4ccc-3cc41)CCO2]

23

(2S)-2-(tert-Butoxy)-2-{4,18-dimethyl-26-oxa-8-thia-14,15,16,34-tetraazaheptacyclo[21.6.2.2$^{10,13}$.1$^{6,9}$.0$^{2,7}$.0$^{12,16}$.0$^{27,31}$]tetratriaconta-1(29),2,4,6,9(34),10,12,14,27,30,32-undecaen-3-yl}acetic acid Example 11

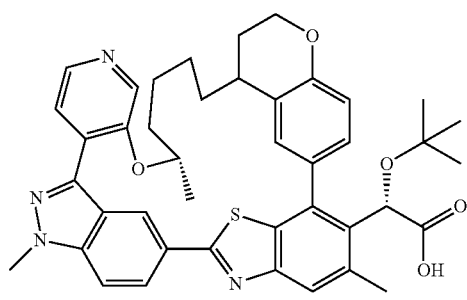 [SMILES: Cc1cc2nc3sc2c(c1[C@H](OC(C)(C)C)C(=O)O)-c1ccc2c(c1)C(CCCC[C@H](C)Oc1cnccc1-c1nn(C)c4ccc-3cc14)CCO2]

(2S)-2-(tert-Butoxy)-2-[(24S)-4,14,24-trimethyl-23,32-dioxa-8-thia-14,15,20,40-tetraazaoctacyclo[27.6.2.2$^{10,13}$.1$^{6,9}$.0$^{2,7}$.0$^{12,16}$.0$^{17,22}$.0$^{33,37}$]tetraconta-1(35),2,4,6,9(40),10,12,15,17(22),18,20,33,36,38-tetradecaen-3-yl]acetic acid Example 12

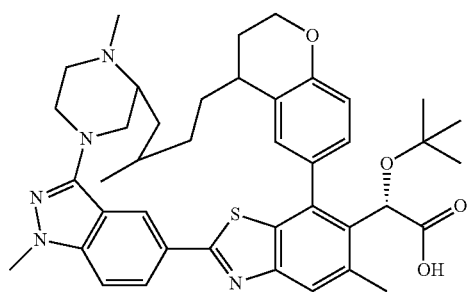 [SMILES: Cc1cc2nc3sc2c(c1[C@H](OC(C)(C)C)C(=O)O)-c1ccc2c(c1)C(CCO2)CCC(C)CC1CN(CCN1C)c1nn(C)c2ccc-3cc12]

(2S)-2-(tert-Butoxy)-2-{4,14,20,23-tetramethyl-29-oxa-8-thia-14,15,17,20,38-pentaazaoctacyclo[24.6.2.2$^{10,13}$.1$^{6,9}$.1$^{17,21}$.0$^{2,7}$.0$^{12,16}$.0$^{30,34}$]octatria-conta-1(32),2,4,6,9(38),10,12,15,30,33,36-undecaen-3-yl}acetic acid Example 13

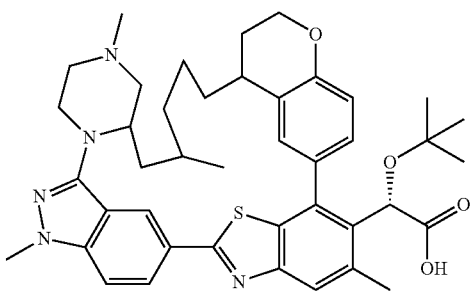 [SMILES: Cc1cc2nc3sc2c(c1[C@H](OC(C)(C)C)C(=O)O)-c1ccc2c(c1)C(CCCC(C)CC1CN(C)CCN1c1nn(C)c4ccc-3cc14)CCO2]

24

(2S)-2-(tert-Butoxy)-2-{4,14,20,24-tetramethyl-31-oxa-8-thia-14,15,17,20,39-pentaazaoctacyclo[26.6.2.2$^{10,13}$1$^{6,9}$.0$^{2,7}$.0$^{12,16}$.0$^{17,22,32,36}$]nonatria-conta-1(34),2,4,6,9(39),10,12,15,32,35,37-undecaen-3-yl}acetic acid Example 14

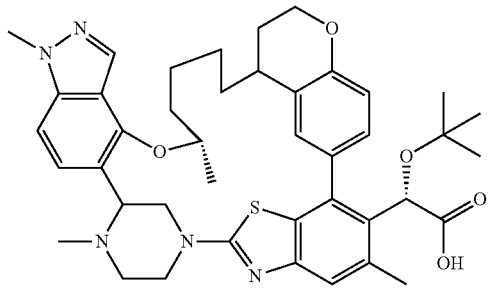 [SMILES: Cc1cc2nc3sc2c(c1[C@H](OC(C)(C)C)C(=O)O)-c1ccc2c(c1)C(CCCC[C@H](C)Oc1c(ccc4c1cnn4C)C1CN3CCN1C)CCO2]

(2S)-2-(tert-Butoxy)-2-[(25S)-4,13,19,25-tetramethyl-24,33-dioxa-8-thia-10,13,19,20,40-pentaazaoctacyclo[28.6.2.1$^{6,9}$.1$^{10,14}$.0$^{2,7}$.0$^{15,23}$.0$^{18,22}$.0$^{34,38}$]tetraconta-1(36),2,4,6,9(40),15(23),16,18(22),20,34,37-undecaen-3-yl]acetic acid Example 15

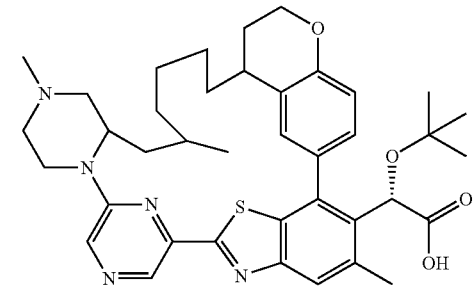 [SMILES: Cc1cc2nc3sc2c(c1[C@H](OC(C)(C)C)C(=O)O)-c1ccc2c(c1)C(CCCCC(C)CC1CN(C)CCN1c1cncc-3n1)CCO2]

(2S)-2-(tert-Butoxy)-2-{4,18,22-trimethyl-30-oxa-8-thia-12,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl}acetic acid Example 16

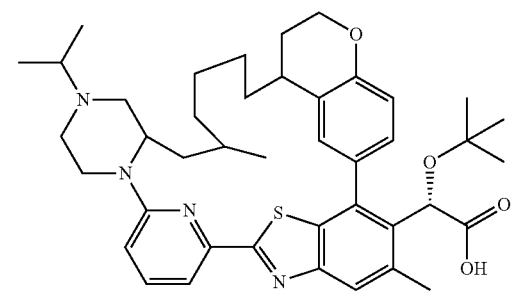 [SMILES: Cc1cc2nc3sc2c(c1[C@H](OC(C)(C)C)C(=O)O)-c1ccc2c(c1)C(CCCCC(C)CC1CN(C(C)C)CCN1c1cccc-3n1)CCO2]

25

(2S)-2-(tert-Butoxy)-2-[4,22-dimethyl-18-(propan-2-yl)-30-oxa-8-thia-15,18,36,37-tetraazaheptacyclo[25.6.2.1⁶,⁹.1¹⁰,¹⁴.0²,⁷.0¹⁵,²⁰.0³¹,³⁵]heptatriaconta-1(33),2,4,6,9(37),10(36),11,13,31,34-decaen-3-yl]acetic acid Example 17

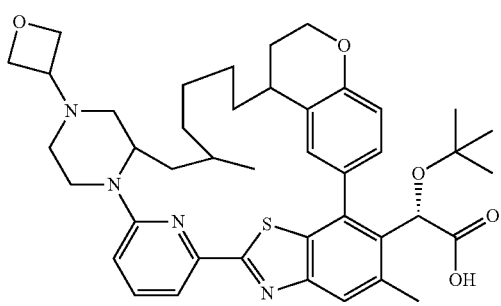 [SMILES: Cc1cc2nc3sc2c(c1[C@H](OC(C)(C)C)C(=O)O)-c1ccc2c(c1)C(CCCCC(C)CC1CN(C4COC4)CCN1c1cccc-3n1)CCO2]

(2S)-2-(tert-Butoxy)-2-[4,22-dimethyl-18-(oxetan-3-yl)-30-oxa-8-thia-15,18,36,37-tetraazaheptacyclo[25.6.2.1⁶,⁹.1¹⁰,¹⁴.0²,⁷.0¹⁵,²⁰.0³¹,³⁵]heptatriaconta-1(33),2,4,6,9(37),10(36),11,13,31,34-decaen-3-yl]acetic acid Example 18

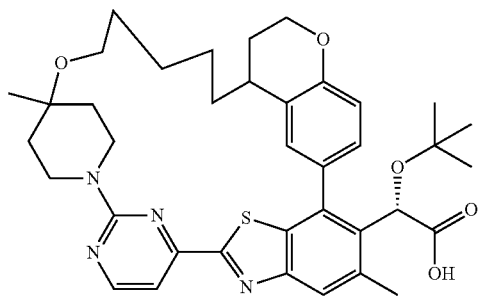 [SMILES: Cc1cc2nc3sc2c(c1[C@H](OC(C)(C)C)C(=O)O)-c1ccc2c(c1)C(CCCCCOC1(C)CCN(CC1)c1nccc-3n1)CCO2]

(2S)-2-(tert-Butoxy)-2-{4,18-dimethyl-19,28-dioxa-8-thia-13,15,36,37-tetraazaheptacyclo[23.6.2.2¹⁵,¹⁸.1⁶,⁹.1¹⁰,¹⁴.0²,⁷.0²⁹,³³]heptatriaconta-1(31),2,4,6,9(37),10(36),11,13,29,32-decaen-3-yl}acetic acid Example 19

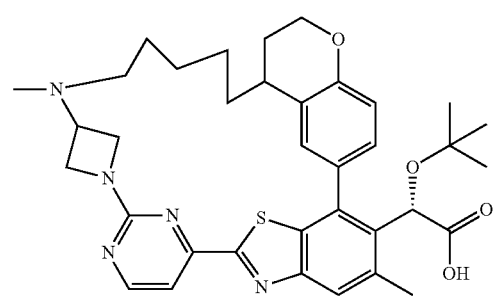 [SMILES: Cc1cc2nc3sc2c(c1[C@H](OC(C)(C)C)C(=O)O)-c1ccc2c(c1)C(CCCCCN(C)C1CN(C1)c1nccc-3n1)CCO2]

26

(2S)-2-(tert-Butoxy)-2-{4,18-dimethyl-27-oxa-8-thia-13,15,18,34,35-pentaazaheptacyclo[22.6.2.1⁶,⁹.1¹⁰,¹⁴.1¹⁵,¹⁷.0²,⁷.0²⁸,³²]pentatriaconta-1(30),2,4,6,9(35),10(34),11,13,28,31-decaen-3-yl}acetic acid Example 20

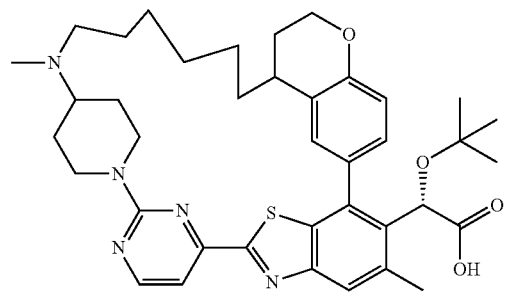 [SMILES: Cc1cc2nc3sc2c(c1[C@H](OC(C)(C)C)C(=O)O)-c1ccc2c(c1)C(CCCCCCN(C)C1CCN(CC1)c1nccc-3n1)CCO2]

(2S)-2-(tert-Butoxy)-2-{4,19-dimethyl-29-oxa-8-thia-13,15,19,37,38-pentaazaheptacyclo[24.6.2.2¹⁵,¹⁸.1⁶,⁹.1¹⁰,¹⁴.0²,⁷.0³⁰,³⁴]octatriaconta-1(32),2,4,6,9(38),10(37),11,13,30,33-decaen-3-yl}acetic acid Example 21

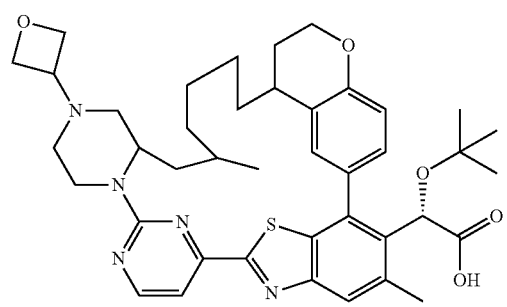 [SMILES: Cc1cc2nc3sc2c(c1[C@H](OC(C)(C)C)C(=O)O)-c1ccc2c(c1)C(CCCCC(C)CC1CN(C4COC4)CCN1c1nccc-3n1)CCO2]

(2S)-2-(tert-Butoxy)-2-[4,22-dimethyl-18-(oxetan-3-yl)-30-oxa-8-thia-13,15,18,36,37-pentaazaheptacyclo[25.6.2.1⁶,⁹.1¹⁰,¹⁴.0²,⁷.0¹⁵,²⁰.0³¹,³⁵]heptatriaconta-1(33),2,4,6,9(37),10(36),11,13,31,34-decaen-3-yl]acetic acid Example 22

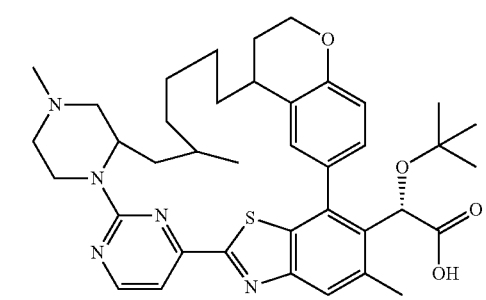 [SMILES: Cc1cc2nc3sc2c(c1[C@H](OC(C)(C)C)C(=O)O)-c1ccc2c(c1)C(CCCCC(C)CC1CN(C)CCN1c1nccc-3n1)CCO2]

(2S)-2-(tert-Butoxy)-2-{4,18,22-trimethyl-30-oxa-8-thia-13,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl}acetic acid Example 23

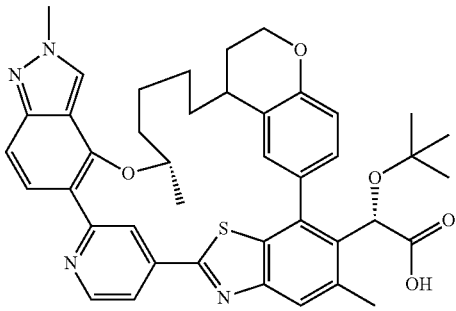 [SMILES: Cc1cc2nc3sc2c(c1[C@H](OC(C)(C)C)C(=O)O)-c1ccc2c(c1)C(CCCC[C@H](C)Oc1c(ccc4nn(C)cc14)-c1cc-3ccn1)CCO2]

(2S)-2-(tert-Butoxy)-2-[(25S)-4,20,25-trimethyl-24,33-dioxa-8-thia-13,19,20,40-tetraazaoctacyclo[28.6.2.1$^{6,9}$.1$^{10,14}$.0$^{2,7}$.0$^{15,23}$.0$^{18,22}$.0$^{34,38}$]tetraconta-1(36),2,4,6,9(40),10(39),11,13,15(23),16,18,21,34,37-tetradecaen-3-yl]acetic acid Example 24

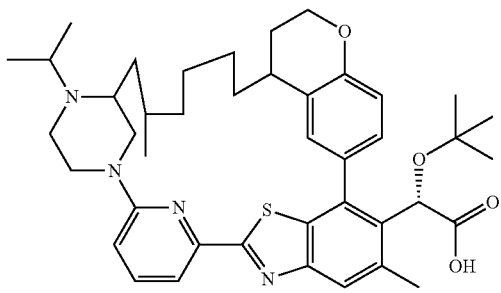 [SMILES: Cc1cc2nc3sc2c(c1[C@H](OC(C)(C)C)C(=O)O)-c1ccc2c(c1)C(CCCCC(C)CC1CN(CCN1C(C)C)c1cccc-3n1)CCO2]

(2S)-2-(tert-Butoxy)-2-[4,21-dimethyl-18-(propan-2-yl)-29-oxa-8-thia-15,18,36,37-tetraazaheptacyclo[24.6.2.1$^{6,9}$.1$^{10,14}$.1$^{15,19}$.0$^{2,7}$.0$^{30,34}$]heptatriaconta-1(32),2,4,6,9(37),10(36),11,13,30,33-decaen-3-yl]acetic acid Example 25

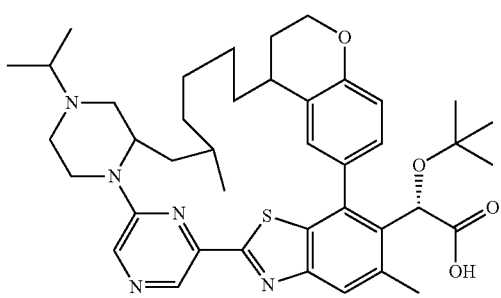 [SMILES: Cc1cc2nc3sc2c(c1[C@H](OC(C)(C)C)C(=O)O)-c1ccc2c(c1)C(CCCCC(C)CC1CN(C(C)C)CCN1c1cncc-3n1)CCO2]

(2S)-2-(tert-Butoxy)-2-[4,22-dimethyl-18-(propan-2-yl)-30-oxa-8-thia-12,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid Example 26

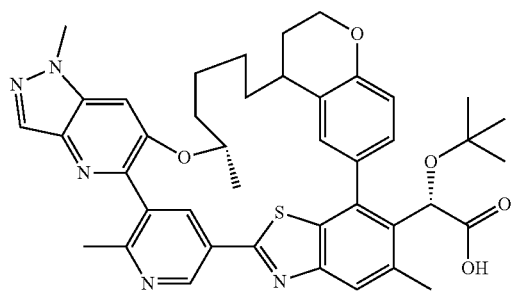 [SMILES: Cc1cc2nc3sc2c(c1[C@H](OC(C)(C)C)C(=O)O)-c1ccc2c(c1)C(CCCC[C@H](C)Oc1cc4c(cnn4C)nc1-c1cc-3cnc1C)CCO2]

(2S)-2-(tert-Butoxy)-2-[(25S)-4,13,20,25-tetramethyl-24,33-dioxa-8-thia-12,16,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

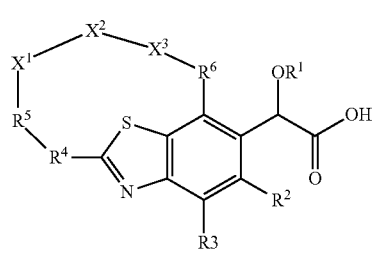

where:
R$^1$ is hydrogen, alkyl, or cycloalkyl;
R$^2$ is hydrogen or alkyl;
R$^3$ is hydrogen, alkyl or halo;
R$^4$ is (R$^7$)-piperazinyl or Ar$^1$;
R$^5$ is absent or Ar$^2$;
or R$^5$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, and oxetanyl;
R$^6$ is cycloalkyl or Ar$^3$;
R$^7$ is hydrogen or alkyl;

Ar$^1$ is phenyl, pyridinyl, pyrazinyl, pyrimidinyl, pyridazinyl, indazolyl, triazolyl, or quinolinyl, and is substituted with 0-3 alkyl substituents;

Ar$^2$ is phenyl, pyridinyl, ((R$^7$)-piperazinyl)pyridinyl, pyrazinyl, pyrimidinyl, pyridazinyl, indazolyl, pyrazolopyridinyl, benzotriazolyl, quinolinyl, or aminoquinolinyl, and is substituted with 0-3 alkyl substituents;

Ar$^3$ is phenyl, chromanyl, or dihydrobenzoxazinyl, and is substituted with 0-3 substituents selected from cyano, halo, alkyl, haloalkyl, alkoxy, and haloalkoxy;

X$^1$ is CH, CH$_2$, O, S, or NR$^7$;

X$^2$ is alkylene or alkenylene; and

X$^3$ is CH, CH$_2$, CH$_2$O, O, S, or NR$^5$;

or a pharmaceutically acceptable salt thereof.

2. A compound of claim 1 where R$^1$ is alkyl; R$^2$ is alkyl; R$^3$ is hydrogen; R$^4$ is Ar$^1$; R$^6$ is chromanyl; X$^1$ is CH$_2$, O, or NR$^7$; X$^2$ is alkylene; and X$^3$ is CH$_2$; or a pharmaceutically acceptable salt thereof.

3. A compound of claim 1 where R$^1$ is alkyl, R$^2$ is alkyl and R$^3$ is hydrogen.

4. A compound of claim 1 where R$^4$ is Ar$^1$.

5. A compound of claim 1 where R$^5$ is Ar$^2$.

6. A compound of claim 1 where R$^5$ is (R$^7$)-piperazinyl.

7. A compound of claim 1 where Ar$^3$ is chromanyl.

8. A compound of claim 1 where X$^1$ is CH$_2$, O, or NR$^7$; X$^2$ is alkylene; and X$^3$ is CH$_2$.

9. A compound of claim 1 selected from the group consisting of (2S)-2-(tert-Butoxy)-2-[(22S)-4,17,22-trimethyl-21,30-dioxa-8-thia-37-azaheptacyclo[25.6.2.1$^{6,9}$.1$^{10,14}$.0$^{2,7}$.0$^{15,20}$.0$^{31,35}$]heptatriaconta-1(33),2,4,6,9(37),10(36), 11,13,15(20),16,18,31,34-tridecaen-3-yl]acetic acid;

(2S)-2-(tert-Butoxy)-2-[(25S)-4,19,21,25-tetramethyl-24,33-dioxa-8-thia-19,20,40-triazaoctacyclo[28.6.2.1$^{6,9}$.1$^{10,14}$.0$^{2,7}$.0$^{15,23}$.0$^{18,22}$.0$^{34,38}$]tetraconta-1(36),2,4,6,9(40),10(39),11,13,15(23),16,18(22),20,34,37-tetradecaen-3-yl]acetic acid;

(2S)-2-(tert-Butoxy)-2-[(25S)-4,20,25-trimethyl-24,33-dioxa-8-thia-12,19,20,39,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid;

(2S)-2-(tert-Butoxy)-2-[(22S)-4,22-dimethyl-18-(4-methylpiperazin-1-yl)-21,30-dioxa-8-thia-13,19,37-triazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,15(20),16,18,31,34-tridecaen-3-yl]acetic acid;

(2S)-2-(tert-Butoxy)-2-[(25S)-4,20,25-trimethyl-24,33-dioxa-8-thia-13,16,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid;

(2S)-2-[(26S)-20-Amino-4,26-dimethyl-25,34-dioxa-8-thia-13,17,41-triazaoctacyclo[29.6.2.1$^{6,9}$.1$^{10,14}$.0$^{2,7}$.0$^{15,24}$.0$^{18,23}$.0$^{35,39}$]hentetraconta-1(37),2,4,6,9(41),10(40),11,13,15(24),16,18(23),19,21,35,38-pentadecaen-3-yl]-2-(tert-butoxy)acetic acid;

(2S)-2-(tert-Butoxy)-2-[(25S)-4,20,25-trimethyl-24,33-dioxa-8-thia-12,13,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid;

(2S)-2-(tert-Butoxy)-2-[4,22-dimethyl-18-(propan-2-yl)-30-oxa-8-thia-13,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid;

(2S)-2-(tert-Butoxy)-2-{4,18-dimethyl-26-oxa-8-thia-14,15,16,34-tetraazaheptacyclo[21.6.2.2$^{10,13}$.1$^{6,9}$.0$^{2,7}$.0$^{12,16}$.0$^{27,31}$]tetratriaconta-1(29),2,4,6,9(34),10,12,14,27,30,32-undecaen-3-yl}acetic acid;

(2S)-2-(tert-Butoxy)-2-[(24S)-4,14,24-trimethyl-23,32-dioxa-8-thia-14,15,20,40-tetraazaoctacyclo[27.6.2.2$^{10,13}$.1$^{6,9}$.0$^{2,7}$.0$^{12,16}$.0$^{17,22}$.0$^{33,37}$]tetraconta-1(35),2,4,6,9(40),10,12,15,17(22),18,20,33,36,38-tetradecaen-3-yl]acetic acid;

(2S)-2-(tert-Butoxy)-2-{4,14,20,23-tetramethyl-29-oxa-8-thia-14,15,17,20,38-pentaazaoctacyclo[24.6.2.2$^{10,13}$.1$^{6,9}$.1$^{17,21}$.0$^{2,7}$.0$^{12,16}$.0$^{30,34}$]octatriaconta-1(32),2,4,6,9(38),10,12,15,30,33,36-undecaen-3-yl}acetic acid;

(2S)-2-(tert-Butoxy)-2-{4,14,20,24-tetramethyl-31-oxa-8-thia-14,15,17,20,39-pentaazaoctacyclo[26.6.2.2$^{10,13}$1$^{6,9}$.0$^{2,7}$.0$^{12,16}$.0$^{17,22,32,36}$]nonatriaconta-1(34),2,4,6,9(39),10,12,15,32,35,37-undecaen-3-yl}acetic acid;

(2S)-2-(tert-Butoxy)-2-[(25S)-4,13,19,25-tetramethyl-24,33-dioxa-8-thia-10,13,19,20,40-pentaazaoctacyclo[28.6.2.1$^{6,9}$.1$^{10,14}$.0$^{2,7}$.0$^{15,23}$.0$^{18,22}$.0$^{34,38}$]tetraconta-1(36),2,4,6,9(40),15(23),16,18 (22),20,34,37-undecaen-3-yl]acetic acid;

(2S)-2-(tert-Butoxy)-2-{4,18,22-trimethyl-30-oxa-8-thia-12,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl}acetic acid;

(2S)-2-(tert-Butoxy)-2-[4,22-dimethyl-18-(propan-2-yl)-30-oxa-8-thia-15,18,36,37-tetraazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid;

(2S)-2-(tert-Butoxy)-2-[4,22-dimethyl-18-(oxetan-3-yl)-30-oxa-8-thia-15,18,36,37-tetraazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid;

(2S)-2-(tert-Butoxy)-2-{4,18-dimethyl-19,28-dioxa-8-thia-13,15,36,37-tetraazaheptacyclo[23.6.2.2$^{15,18}$.1$^{6,9}$.1$^{10,14}$.0$^{2,7}$.0$^{29,33}$]heptatriaconta-1(31),2,4,6,9(37),10(36),11,13,29,32-decaen-3-yl}acetic acid;

(2S)-2-(tert-Butoxy)-2-{4,18-dimethyl-27-oxa-8-thia-13,15,18,34,35-pentaazaheptacyclo[22.6.2.1$^{6,9}$.1$^{10,14}$.1$^{15,17}$.0$^{2,7}$.0$^{28,32}$]pentatriaconta-1(30),2,4,6,9(35),10(34),11,13,28,31-decaen-3-yl}acetic acid;

(2S)-2-(tert-Butoxy)-2-{4,19-dimethyl-29-oxa-8-thia-13,15,19,37,38-pentaazaheptacyclo[24.6.2.2$^{15,18}$.1$^{6,9}$.1$^{10,14}$.0$^{2,7}$.0$^{30,34}$]octatriaconta-1(32),2,4,6,9(38),10(37),11,13,30,33-decaen-3-yl}acetic acid;

(2S)-2-(tert-Butoxy)-2-[4,22-dimethyl-18-(oxetan-3-yl)-30-oxa-8-thia-13,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid;

(2S)-2-(tert-Butoxy)-2-{4,18,22-trimethyl-30-oxa-8-thia-13,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl}acetic acid;

(2S)-2-(tert-Butoxy)-2-[(25S)-4,20,25-trimethyl-24,33-dioxa-8-thia-13,19,20,40-tetraazaoctacyclo[28.6.2.1$^{6,9}$.1$^{10,14}$.0$^{2,7}$.0$^{15,23}$.0$^{18,22}$.0$^{34,38}$]tetraconta-1(36),2,4,6,9(40),10(39),11,13,15(23),16,18,21,34,37-tetradecaen-3-yl]acetic acid;

(2S)-2-(tert-Butoxy)-2-[4,21-dimethyl-18-(propan-2-yl)-29-oxa-8-thia-15,18,36,37-tetraazaheptacyclo[24.6.2.2$^{6,9}$.1$^{10,14}$.1$^{15,19}$.0$^{2,7}$.0$^{30,34}$]heptatriaconta-1(32),2,4,6,9(37),10(36),11,13,30,33-decaen-3-yl]acetic acid;

(2S)-2-(tert-Butoxy)-2-[4,22-dimethyl-18-(propan-2-yl)-30-oxa-8-thia-12,15,18,36,37-pentaazaheptacyclo[25.6.2.1$^{6,9}$.1$^{10,14}$.0$^{2,7}$.0$^{15,20}$.0$^{31,35}$]heptatriaconta-1(33),2,4,6,9(37),10(36),11,13,31,34-decaen-3-yl]acetic acid; and (2S)-2-(tert-Butoxy)-2-[(25S)-4,13,20,25-tetramethyl-24,33-dioxa-8-thia-12,16,19,20,40-pentaazaoctacyclo[28.6.2.1$^{6,9}$.1$^{10,14}$.0$^{2,7}$.0$^{15,23}$.0$^{17,21}$.0$^{34,38}$]tetraconta-1(36),2,4,6,9(40),10(39),11,13,15(23),16,18,21,34,37-tetradecaen-3-yl]acetic acid or a pharmaceutically acceptable salt thereof.

10. A composition useful for treating HIV infection comprising a therapeutic amount of a compound of claim 1 and a pharmaceutically acceptable carrier.

11. A method for treating HIV infection comprising administering a therapeutically effective amount of a compound of claim 1, or a pharmaceutically acceptable salt thereof, to a patient in need thereof.

* * * * *